United States Patent [19]

Shetty

[11] Patent Number: 4,668,510

[45] Date of Patent: * May 26, 1987

[54] IODOPHOR COMPOSITION

[75] Inventor: Bola V. Shetty, Stamford, Conn.

[73] Assignee: Euroceltique, S.A., Luxembourg, Luxembourg

[*] Notice: The portion of the term of this patent subsequent to Mar. 18, 2003 has been disclaimed.

[21] Appl. No.: 818,559

[22] Filed: Jan. 10, 1986

Related U.S. Application Data

[63] Continuation of Ser. No. 638,558, Aug. 7, 1984, Pat. No. 4,576,818.

[51] Int. Cl.$^4$ .................... A61K 31/74; A61K 33/18
[52] U.S. Cl. ...................................... 424/78; 424/150
[58] Field of Search .................................. 424/150, 78

[56] References Cited

U.S. PATENT DOCUMENTS

| | | | |
|---|---|---|---|
| 3,928,581 | 12/1975 | Dahlberg et al. | 424/180 |
| 4,401,651 | 8/1983 | Knutson | 424/80 |
| 4,459,280 | 7/1984 | Colliopoulos | 424/35 |
| 4,470,975 | 11/1984 | Berger et al. | 424/180 |
| 4,576,818 | 3/1986 | Shetty | 424/150 |

Primary Examiner—Leonard Schenkman
Attorney, Agent, or Firm—Steinberg & Raskin

[57] ABSTRACT

New iodophors are provided which exhibit effective degerming of skin, nucous membranes of animals and surfaces of inanimate objects and which provide broad spectrum microbicidal action without toxicity or irritation. The iodophors of the invention are complexes of iodine with polydextrose or with the polymer resulting from the copolymerization of sucrose and epichlorohydrin. The invention further relates to germicidal compositions containing such complexes and to methods of producing the complexes.

5 Claims, No Drawings

IODOPHOR COMPOSITION

BACKGROUND OF THE INVENTION

Iodine is a non-metallic element of the halogen family, and is the only halogen that is solid at ordinary temperatures. Iodine has been shown to have a range in valence of from $-1$ to $+7$, and compounds thermodynamically stable with respect to their constituent elements are known to exist for all of the oxidation states of iodine.

Iodine was discovered early in the 19th century, and the first practical therapeutic application of iodine was as a remedy for goiter. This use was followed shortly thereafter with use as a germicide for treatment of wounds. It was during the American war between the states that the first wide-spread use of iodine as an antiseptic and germicide was developed for the treatment of battle wounds. Since that time, iodine has been recognized to be a preferred germicide, but because of certain inherent chemical, physical and biological properties, the antiseptic degerming use of iodine for humans and animals has been limited.

Elemental iodine has a high vapor pressure which results in pharmaceutical compositions having varying germicidal potency, since the iodine content volatilizes from an antiseptic preparation upon aging. Moreover, the high vapor pressure of iodine limits its use in closed compartments, such as body cavities or under a bandage, because of the corrosive destruction and irritation of skin, mucous membranes, and other vital tissues by the elemental iodine itself. While the overall systemic toxicity of iodine is low, fatalities have occurred after accidental ingestion of iodine solutions. However, the pathological changes recorded for fatal cases of iodine poisoning are largely the result of tissue hypoxia and local corrosive destructive effects, rather than systemic iodine poisoning.

Another limitation for the germicidal use of iodine is its high aqueous insolubility (0.034% at 25° C.). While the aqueous solubility of iodine may be increased through the use of alcohol (as for example, tincture of iodine) or through the use of inorganic metallic salts as solubilizing agents (as for example, sodium iodide and/or potassium iodide in the preparation of Lugols' Solution), such iodine solutions also possess the same toxic tissue manifestation which generally limit the use of iodine germicidal solutions.

When alcohol is used as a solvent for iodine, the use of such preparations on abraded and injured skin or mucous membrane is painful and damaging. Further, as the alcohol evaporates, the iodine content concentrates which increases the incidence of burning, corrosive destruction, and staining of tissues.

Metallic iodides have been used to solubilize elemental iodine in water through the direct formation of a water-soluble iodine complex formed between the diatomic iodine ($I_2$) and the iodide ion ($I^-$) to form $I_3^-$ ions. Such aqueous iodine solutions have not modified the toxic tissue reactions of elemental iodine, so that burning and staining still occur. In fact, such undesirable reactions are now more frequent, since larger concentrations of elemental iodine are utilized to prepare the aqueous iodine germicidal compositions.

Iodine in aqueous solution dissociates to equilibrium as follows:

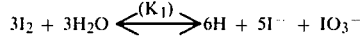

with the equilibrium constant ($K_1$) being about $4 \times 10^{-46}$ depending upon the temperature. In aqueous media, the dissociation phenomena for diatomic iodine is further complicated by the formation of several species of iodide ion, the most significant of which is the tri-iodide ion. The equilibrium constant ($K_2$) is approximately $7.5 \times 10^2$ for the following reaction:

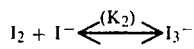

It is preferable to combine these equilibrium reactions when describing the dissociation of diatomic iodine in aqueous solutions as:

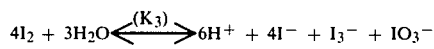

with the equilibrium constant ($K_3$) being approximately $3 \times 10^{-43}$.

Iodine is a mild oxidizing agent in acidic solution, with a redox equilibrium potential of 0.534 V at 25° C. for the iodine-iodide ion couple. Iodine will readily oxidize sulfite to sulfate, and thiosulfate to tetrathionate, while ferric and cupric salts are reduced in acidic solution by the iodide ion, to form free iodine. In dilute solutions, iodine completely oxidizes sulfur dioxide to sulfuric acid, whereas iodides reduce sulfuric acid to sulfur dioxide, sulfur and even hydrogen sulfide, with the liberation of free iodine. In neutral or slightly alkaline aqueous solutions, iodine exerts a somewhat stronger oxidizing action because of the formation of hypoiodite ion, in accordance with the following reaction:

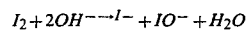

Such aqueous solutions are strong iodinating agents, and cause redox changes in body proteins and other biological substances within the alkaline physiologic pH range. Iodine will add to unsaturated linkages in tissue proteins, to cause denaturation which interrupt essential physiological reactions.

In an effort to overcome the noxious tissue toxicity observed for aqueous and hydroalcoholic solutions of iodine, while at the same time maintaining the germicidal and microbicidal activity of elemental iodine, water-soluble organic complexes of iodine with organic polymers were prepared. Combinations of elemental iodine and certain organic polymers, as for example polyvinylpyrrolidone and detergent polymers, has been shown to increase the aqueous solubility of elemental iodine. Such polymer-iodine complexes were termed iodophors.

The organic polymers used to form an iodophor comprise a broad range in molecular weight and chain length, and may be either ionic or nonionic in character, as well as possessing either surfactant or non-surfactant properties. A loose bond forms between the iodine and organic polymer to form the complex or iodophor, and aqueous solutions of up to 30% by weight in iodine content may be prepared (all percents are by weight herein, except as otherwise noted).

The general class of organic iodophor compounds comprises two distinct polymer groups: Polyvinylpyrrolidone, a non-detergent, non-ionic and non-surface active polymer; and a broad variety of detergent/surface-active polymers, including non-ionic, anionic, and cationic surface-active polymers. Both polymer groups are complexed with elemental iodine to form the iodophor. Anionic surface-active agents are generally not capable of providing stable iodine complexes. However, certain anionic surface-active agents, such as enumerated in U.S. Pat. No. 3,039,916, have been found to be suitable for forming iodine complexes for germicidal use.

Non-detergent, non-ionic organic polymers have generally not been employed as a carrier for iodine in germicidal use. Only one such polymer, polyvinylpyrrolidone, has to date been found satisfactory to complex with iodine to form useful iodophor germicidal compositions. Polyvinylpyrrolidone is a non-ionic, non-detergent, water-soluble synthetic organic polymer characterized by its unusual complexing ability and colloidal properties together with physiological inertness. The commonly employed, polyvinylpyrrolidone-iodine (PVP-I) complex contains from about 9 to 12% of titratable iodine, although polymer iodine complexes with both greater and lesser amounts of iodine are known. Polyvinylpyrrolidone iodine is a highly-effective germicide, providing a broad spectrum of microbicidal action against virtually all microbes.

Polyvinylpyrrolidone-iodine (PVP-I) exhibits low systemic toxicity, and is essentially non-irritating to mammalian tissue, in addition to being non-sensitizing and not causing pain when applied to wounds or mucous membrane.

Thus polyvinylpyrrolidone iodone (PVP-I) is extensively used as in important germicidal agent in man and animals, as well as in environmental uses. Polyvinylpyrrolidone iodine and the preparation thereof is described in U.S. Pat. No. 2,739,922. However, no other member of the non-detergent, non-ionic class of organic polymers has been found to be suitable for such antiseptic purposes.

The general method of preparing an iodophor complex is to bring the elemental diatomic iodine into intimate contact with the selected polymer either in the dry or powder form, or in the presence of a suitable solvent. Heat may be used to accelerate formation of the complex. Upon completion of the reaction, the iodophor complex of the respective polymeric carrier with iodine is obtained in certain reproducible proportions of one to the other.

Studies have demonstrated that the microbicidal potency of iodophor germicidal preparations is essentially the same as that known for aqueous and/or alcoholic solutions of elemental iodine, despite the modified tissue toxicity of the iodophors. Superiority of iodophor germicidal preparations over the aqueous and/or alcoholic inorganic elemental iodine solutions have been demonstrated to reside essentially in decreased toxicity, reduced tissue irritation, lowered iodine vapor pressure, as well as in the non-staining feature of skin and natural fabrics of the iodophor preparations.

Iodophor preparations are described in terms of available or titratable iodine which is considered to be the iodine released from the complex to exert its germicidal activity. However, such available iodine determinations do not either reflect the total iodine content of the iodophor or its germicidal potency.

As noted above, the most suitable polymer for the formation of iodophors is polyvinylpyrrolidone, which is the only nondetergent, nonionic organic polymer suitable for the formation of antiseptic iodophors.

SUMMARY OF THE INVENTION

It is accordingly a primary object of the present invention to provide a new nondetergent, nonionic polymer which can form complexes with elemental iodine to provide highly effective iodine-containing germicidal preparations.

It is another object of the present invention to provide nonionic, nondetergent organic carbohydrate polymers which complex with elemental iodine to give effective iodophor preparations.

It is yet another object of the present invention to provide new nonionic, nondetergent iodophor preparations and germicidal and antiseptic compositions thereof.

It is still another object of the present invention to provide methods of producing the new iodophors of the invention.

Other objects and advantages of the present invention will be apparent from a further reading of the specification and of the appended claims.

With the above and other objects in view, the present invention mainly comprises complexes of iodine with polydextrose or with the carbohydrate polymer produced by the copolymerization of sucrose and epichlorohydrin.

Polydextrose is a non-nutritive, polysaccharide, carbohydrate polymer prepared by the condensation polymerization of saccharides in the presence of polycarboxy acid catalysts, under reduced pressure. Polydextrose is described in U.S. Pat. Nos. 3,766,105 and 3,786,794, and is available from Pfizer, Inc., New York, N.Y.

Polydextrose is a white-to-tan powder occurring in both water soluble and water insoluble forms. The average molecular weight for polydextrose is from about 1,500 to 36,000, with water soluble polydextrose having an average molecular weight of about 2,500 to 18,000 and water insoluble polydextrose having an average molecular weight of between 6,000 to 36,000. When the number average molecular weight of polydextrose is determined by the modified reducing end group method of Isbel (J. Res. Nat'l. Bur. Standards 24, 241 (1940)), the average molecular weight of polydextrose will usually range from about 1,000 to 24,000, with most of the molecular weight falling within the range of from 4,000 to 12,000. When the modified reducing end group method is used to determine the number average molecular weight of polydextrose, the number average weight has been shown to be a multiple of 1.5 of the number average molecular weight found by the modified reducing and group method of Isbel. However, any one of the well known methods for polymer molecular weight determination may be used to characterize the number average molecular weight for polydextrose.

It is clear from the schematic formula of polydextrose (provided by Pfizer) that primarily 1-6 linkages predominate because of the reactivity of the primary hydroxy groups, although other glucosidic linkages may occur. In the soluble form of polydextrose, each of the present acid moieties is esterified to the polydextrose, however when the acid moiety is esterified to more than one polydextrose moiety, cross-linking will occur. Synthetic polydextrose is not affected by amylolytic enzymes, while animal nutrition and radioactive tracer studies have demonstrated that polydextrose is substantially non-toxic.

The usually commercially available polydextrose polymer is a low molecular weight, water-soluble, randomly bonded polymer of glucose containing minor amounts of sorbitol end groups and citric acid residues attached to the polymer by mono- and di-ester bonds. The effect of the random bonding and occasional di-ester cross-linking in polydextrose, is a polymer more resistant to acid or enzyme hydrolysis than other carbohydrate polymers such as starch.

The average molecular weight of commercially-available polydextrose is 1,500, ranging from 162 to approximately 20,000. This molecular weight range ensures a high degree of water-solubility and relatively low viscosity, with principal properties similar to sucrose but without the sweetness in taste. The molecular weight range for commercially available polydextrose is:

| MOLECULER WEIGHT RANGE | PERCENT |
| --- | --- |
| 162–5,000 | 88.7 |
| 5,000–10,000 | 10.0 |
| 10,000–16,000 | 1.2 |
| 16,000–18,000 | 0.1 |

Polydextrose contains trace amounts of 5-hydroxymethylfurfural and a small amount of levoglucosan (1–6 anhydroglucose), in addition to smaller amounts of unreacted starting ingredients such as glucose, sorbitol, and citric acid.

When polydextrose polymer is combined with elemental iodine, the resultant polydextrose-iodine complex (PDI) is formed. This polydextrose iodine complex is a tan-to-amber colored powder which starts to melt at about 93° C., and by 127° C., completely forms a red liquid. Polydextrose iodine powder is highly soluble in water, and at room temperature results in a reddish-brown colored aqueous solution containing as much as 80% by weight of polydextrose iodine. Solutions of even greater concentration may be prepared. This increased water solubility contrasts sharply with the well known aqueous insolubility of iodine which is soluble in water only to the extent of 0.034%. This increased water solubility establishes that complexing has occurred during the reaction of polydextrose with iodine to form a new compound which has new and advantageous properties. Aqueous solutions of polydextrose-iodine (PDI) are acidic in nature, but may be buffered over the entire physiological acid pH range, without interfering with complex formation or germicidal action.

The infrared spectrum of polydextrose iodine utilizing the potassium bromide (KBr) pellet technique over the range of from $4,000^{cm-1}$ to $200^{cm-1}$ reveals a very slight shoulder with an increased intensity of the peak at $800^{cm-1}$ $300^{cm-1}$. When polydextrose iodine is dissolved in water the titratable iodine content may be determined by the well known method of iodine titration with sodium thiosulfate solution.

The tests have determined that polydextrose iodine provides sufficient equilibrium iodine for germicidal purposes so that the substance is an effective germicide.

Conductance tests carried out on polydextrose iodine have confirmed that the polydextrose is definitely complexed with triiodide ($I^{-3}$) and/or iodide ($I^{-}$) because the equivalence conductance at zero concentration is significantly less than that for iodine solution (Lugol's Solution). It has further been noted that the ratio of free ions to bound ions, as the concentration decreases, is constant. Polydextrose iodine shows lower free ions concentration than iodine solution.

In accordance with the further embodiment of the present invention, complexes are provided of iodine with the polymer produced by the copolymerization of sucrose and epichlorohydrin. The molecules of such polymer have a branched structure and a high content of hydroxyl groups which results in a very good solubility in aqueous media of the polymer.

Such polymers obtained by the copolymerization of sucrose epichlorohydrin have been marketed by Pharmacia Fine Chemicals AB of Uppsala, Sweden under the name "Ficoll", and for convenience of discussion in the specification hereof, reference will be made to Ficoll rather than to the "polymer prepared by copolymerization of sucrose and epichlorohydrin".

The molecules of Ficoll have a branch structure, with a high content of hydroxyl groups resulting in very good solubility in aqueous media. There are no ionized groups present in Ficoll, as this is also a non-ionic, non-detergent, nonsurfactant organic carbohydrate polymer as polydextrose. The preparation and properties of Ficoll may be found in "Ficoll For Cell Research" published by Pharmacia Fine Chemicals. The Ficoll-Iodine complex exhibits the same properties as the PDI complex with respect to germicidal activity and delivery of iodine. With the determination of equilibrium and method for delivery being determined by the same methods as for the PDI complex.

Both the polydextrose-iodine (PDI) and Ficoll-Iodine (FI) complexes provide for smooth, even, delivery of antiseptic iodine when applied to living or inanimate surfaces, over a period of time, without any irritability or toxicity effects. This is a tremendous improvement over any of the previously known inorganic iodine-containing germicidal preparations, which either result in high toxicity, skin or surface irritation, or lack of control of delivery of the antiseptic iodine over a period of time.

As previously noted, it was totally unexpected that any non-detergent, non-ionic, non-surfactant organic polymers other than polyvinylpyrrolidone would be suitable for preparation of an iodophor complex. However, it has now been found that polydextrose and Ficoll polymer are both suitable for preparing the requisite complexes, for adequate, effective, delivery of germicidal action. In addition to forming similar complexes to PVP-I, both polydextrose polymer and Ficoll polymer have a greater water-solubilizing effect on elemental iodine than polyvinylpyrrolidone, the elemental iodine having a very low solubility in water. Thus, the polymer iodine complexes of PDI and FI have practically no free elemental iodine in the solid state when subjected to an extraction with n-heptane, since the complexed iodine in the PDI or the FI complexes is in tri-iodide anionic equilibrium which is insoluble in n-heptane and other organic solvents.

DETAILED DESCRIPTION OF PREFERRED EMBODIMENTS

The following is a more detailed description of the present invention which is merely intended as exemplary, and not as limiting the scope of the invention in any way.

As noted above, polydextrose is a water soluble, randomly bonded polymer of D-glucose containing minor amounts of sorbitol end groups and citric acid residues attached to the polymer by mono and di-ester linkage. Polydextrose contains every possible type of glucosidic linkage. Because of the reactivity of the primary hydroxy groups, the 1-6 bonding predominates in polydextrose. The result of this random bonding and occasional di-ester cross-linking is a polymer more resistant to acidic or enzyme hydrolysis than a polymer such as starch.

Synthesis of polydextrose polymer, as noted above, is disclosed in U.S. Pat. Nos. 3,766,165 and 3,876,794, while the polymer itself is available from Pfizer. Previous known uses include that of a multipurpose food additive, such as a reduced caloric bulking agent. Such use includes additives to baked goods, chewing gum, confections, salad dressings, dairy products, hard candy, etc., and other types of edible products. Overall, polydextrose is stable over time, however long term storage at elevated temperatures can result in some discoloration.

Polydextrose forms a clear melt above 130° C., in a similar manner to sucrose. Polydextrose type N available from Pfizer is a clear, straw-colored 70% solution prepared by partially neutralizing polydextrose with potassium hydroxide. Viscosity of this particular solution of polydextrose type N is somewhat greater than that of sugar or sorbitol solutions of equal concentrations. Polydextrose can also function as a humectant, with the powder absorbing moisture under normal atmospheric conditions until equilibrium is reached. A 10% W/V aqueous solution of polydextrose has a pH of about 2.5 to 3.5.

Safety of polydextrose has been established by 32 different studies in five species of animals and in 8 human studies. Most of the polydextrose product passes through a living body unabsorbed. The principal utilization pathway for the remainder thereof involves metabolism by intestinal micro-organism to form carbon dioxide and volatile fatty acids which can then be absorbed and utilized as an energy source source by a living body. Use of polydextrose has been approved by the FDA which defines the same as a partially metabolizable water-soluble polymer prepared from D-glucose with small amounts of sorbitol and citric acid. Polydextrose may be partially neutralized with potassium hydroxide.

When 0.10 g polydextrose is dissolved in 25 ml of water and analyzed for ultraviolet (UV) characteristics, the absorbence spectrum from 800-190 nm is obtained. Two peaks are observed in the region 190-300 nm with maxima at 193 nm and 281 nm. The absorbence intensity is 2.87 and 0.144 respectively.

Concerning the infrared spectrum, percent transmission is measured for a polydextrose-KBr pellet over an infrared spectrum from 400-200 $cm^{-1}$. Four regions of infrared absorbence are observed, namely 3450-2500 $cm^{-1}$, 1800-1200 $cm^{-1}$, 1200-800 $cm^{-1}$, and 800-300 $cm^{-1}$. One broad peak of strong intensity with a narrow weaker shoulder at 2970 $cm^{-1}$, a moderate, fairly broad peak at 1600 $cm^{-1}$, and a strong, fairly broad peak at 1000 $cm^{-1}$ are all observed.

Viscosity of polydextrose as a function of its concentration, was determined by preparing varying solutions of polydextrose containing from 1% w/v to 60% w/v. The relative viscosities of these solutions were determined at 25° C. and plotted as a function of concentration. Also, the viscosity of polydextrose, as compared to sorbitol and sucrose, is shown in the following Table I:

TABLE I

| % POLYMER W/W | VISCOSITY (CENTIPOISES) | | |
|---|---|---|---|
| | SORBITOL | SUCROSE | POLYDEXTROSE |
| 10% | — | — | 10 |
| 30% | — | — | 15 |
| 40% | — | — | 24 |
| 50% | 10 | 24 | 46 |
| 60% | 24 | 40 | 100 |
| 70% | 120 | 300 | 800 |

The above determined viscosities are available from Pfizer.

Ficoll, has an average molecular weight of 400,000±100,000, an intrinsic viscosity of about 0.17 dl/g, and a specific rotation $[\alpha]^{20}_D$ of +56.5°. There is less than 1% dialysable material in polysaccharide Ficoll polymer, including the sodium chloride present therein. Reactivity and stability of Ficoll are determined by the hydroxy groups and the glycosidic groups present in the sucrose residues therein. Ficoll is stable in both alkaline and neutral solutions. At pH values lower than 3, Ficoll is rapidly hydrolized, especially at elevated temperatures. However, Ficoll can be sterilized in neutral solutions by autoclaving at 110° C. for 30 minutes without degradation.

As available from Pharmacia Fine Chemicals, Ficoll is delivered as a spray-dried powder and thus readily soluble in aqueous media, when added slowly with concomitant stirring. Concentrations of up to 50% w/v of Ficoll in solution can be obtained. The relative viscosities of Ficoll solution are at various concentrations are illustrated in Table II below:

TABLE II

| FICOLL PERCENT (w/v) | 10 | 20 | 30 | 40 | 50 |
|---|---|---|---|---|---|
| $n_r$ at 20° | 5 | 20 | 60 | 80 | 600 |

Unike sucrose itself Ficoll solutions have low osmotic pressure, while densities of sucrose and Ficoll are comparable. Because of high molecular weight and low content of dialyzable material, Ficoll has a much lower permeability toward cell membranes than sucrose, for example. Ficoll has previously been used primarily in the field of centrifugation in dense media, where Ficoll has been used for separation and isolation of cells and subcellular particles. Ficoll may also be used as a stabilizing agent in protein solutions, and in dialysis.

Other compatible ingredients may be incorporated into the iodophor preparation formed from iodine and either polydextrose or Ficoll's polymer. Such compatible ingredients include buffers, supplementary surfactants, and additional non-aqueous solvent. An example of such solvent is glycerin.

The amount of iodine that can be incorporated in the new iodophors of the present invention, that is the iodophors of polydextrose or of Ficoll polymer would be the same as in the case of other known iodophors such as polyvinylpyrrolidone iodine. In general, the amount of iodine is between 1-20%, preferably 2-16%, most preferably 2-10%.

The complex of polydextrose and/or polysaccharide Ficoll polymer with iodine may be prepared through the interaction of elemental iodine with polydextrose and/or Ficoll polymer in its solid state. The rate of such reaction (formation of the requisite complex) may be determined by controlling the temperature. Such a reaction will proceed slowly at room temperature, and will be accelerated at elevated temperatures. The complex is preferably prepared by initially dissolving the requisite quantity of polydextrose or Ficoll polymer in a polar solvent such as water, followed by addition of elemental iodine under vigorous stirring until dissolution is complete. Elemental iodine may be introduced into such a polar solvent in the form of an aqueous solution itself, such as Lugols Solution, or as an aqueous solution of sodium iodide-iodine.

Other suitable solutions for the introduction of iodine into the polar solvent to form the iodophor preparation, include potassium iodide-iodine, and hydriodic acid solutions. In this instance, the advantageous iodophor preparation results from the interaction of the elemental iodine, alkali metal iodide and polydextrose and/or Ficoll polymer in the polar solvent, e.g. water solution. In this manner, polydextrose iodine preparations may be prepared with up to about 20% by weight of iodine based upon the weight of polydextrose polymer utilized.

The various other adjuvants may also be dissolved in the polar solvent during formation of the PDI complex, adjuvants such as the buffer, surfactant, glycerine, etc. After all the requisite components have been incorporated into solution, and the solution adequately stirred for a sufficient period of time such as 30 minutes, then the solution may be cooled if necessary, optionally filtered, and freeze-dried to prepare crystals or powders of the PDI iodophor complex. The iodine may be incorporated into the polydextrose solution in any number of ways, such as by simultaneous addition of an alkali metal iodide solution, followed by hydriodic acid addition in a small amount. After the solution has been suitably prepared and freeze-dried, the complex may be assayed for available iodine. The iodophor preparation may also be assayed for available iodine content after a certain period of time, e.g. several weeks, to make certain that the effectiveness of the preparation does not dissipate over time. Other suitable polar solvents that may be used for the preparation of the iodophor complex include alcohol, in addition to the water, and any mixture of these.

Polydextrose iodine powder is very water-soluble at room temperature. Such a solution has a reddish-brown color. Iodine availability in the aqueous solution of the iodophor, may be determined by direct titration with standardized sodium thiosulfate solution. This is a classic oxidation-reduction type reaction conventionally used in iodine chemistry. For example, polydextrose iodine complex (PDI iodophor) with a 7.45% available iodine content, exhibits a solubility of about 81% in water. A polydextrose iodine complex with 3.25% available iodine, also exhibits a solubility of about 81% in water.

Melting points of various polydextrose-iodine complexes have also been determined. Such samples have been previously dried under vacuum and over $P_2O_5$ for 16 hours. The results of melting point determinations for the various samples were as follows:

| SAMPLE | MELTING POINT (°C.) | OBSERVATIONS |
| --- | --- | --- |
| 7.45% available iodine | 97–127 | Melts into a dark red liquid. |
| 3.25% available iodine | 93–127 | Melts into a red liquid. |
| Polydextrose alone | 115–130 | Melts into a clear liquid. |

The polydextrose-iodine complexes exhibit an increased temperature range over which melting begins and ends. The melting point is also slightly depressed, as compared with the polydextrose control alone. Such melting point determination was carried out in a Thomas Hoover Capillary Melting Point Apparatus. The melting point of elemental iodine itself, is 113.6° C.

In the preparation of iodophors in general, several factors affect the quality and efficacy of the preparations. For example, the amount of iodide ion present in solution critically affects the overall stability of the iodophor preparation. Rate of the decomposition of elemental iodine in solution is inversely proportional to the iodide ion concentration. Moreover, an increase in pH of the preparation reduces the overall stability of the iodophor, while the increase in iodide ion content has the reverse effect, in other words increases stability of the iodophor. Furthermore, the strength of the bond formed between the elemental iodine and the polydextrose or Ficoll polymer or the matrix thereof, plays a critical roll in determining the velocity of liberation of iodine from the polymer depot or the matrix thereof, to the receptor site.

Various iodophor preparations, namely polydextrose iodine complex (PDI) and polyvinylpyrrolidone iodine complex (PVP-I) were prepared using the respective polymers polydextrose and polyvinylpyrrolidone (PVP-K30), with elemental iodine or Lugol's Solution. Polyvinylpyrrolidone PVP-K30 is a comparatively high molecular weight polymer with at least 95% thereof having a weight average molecular weight of 40,000. This particular polymer, when reacted with iodine, results in the complex of polyvinylpyrrolidone iodine as noted supra. This particular complex is soluble in water and when applied to a wound, acts as an antibacterial agent. The rate and velocity of release of iodine from the polymer depot is determined by the strength of the bond between the iodine and the polymer, and also by the pH of the formulation.

Several such formulations with varied strength of available iodine were prepared with the respective polydextrose iodine (PDI) and polyvinylpyrrolidone iodine (PVP-I) complexes, with antibacterial activity thereof being compared using various microorganisms. Four such formulations using PDI, surfactant, glycerin, and buffer, were prepared at pH of about 5. The available iodine content in these preparations varied from 2.0%, 1.0%, 0.25%, to 0.1%. Additionally, four samples were prepared using only the buffer adjuvant, having the same strength of available iodine as the initial four preparations and a pH of also about 5.

Additionally, four formulations of polyvinylpyrrolidone iodine (PVP-I) complex were also prepared, using the PVP-I, surfactant, glycerin, and buffer, also at a pH of about 5. Available iodine content in the PVP-I preparations also vary from 2.0%, 1.0%, 0.25%, to 0.1%. Also, four additional samples were prepared using only the buffer, with the same requisite strengths of available iodine and pH of about 5.

The following microorganisms were used for antibacterial evaluation:

*Staphylococcus aureus* #1(ATCC 6538) penicillin sensitive
*Staphylococcus aureus* #4 (GBL) penicillin resistant
*Staphylococcus aureus* #30 (GBL-CDC) toxic shock strain
*Staphylococcus epidermidids* (GBL) normal skin flora
Spores of *B. fumilus* E601.

The application of the respective iodophor preparations upon the concomitant bacteria samples was carried out. The specific compositions that were examined in the testing were as follows:

PDI COMPLEX 2.0% AVAILABLE $I_2$ 27.78 g PDI Complex
30.0 g Glycerin
0.25 g Alipal CO-436 (surfactant)
1.119 g Buffer
Water to 100 cc.

PDI COMPLEX WITH 1% AVAILABLE $I_2$ 13.89 g Polydextrose Iodine
30.0 g Glycerin
0.25 g Alipal CO-436
0.56 g Buffer
Water to 100 cc.

PDI COMPLEX WITH 0.25% AVAILABLE $I_2$ 3.47 g Polydextrose Iodine
30.00 g Glycerin
0.25 g Alipal CO-436
0.140 g Buffer
Water to 100 cc.

PDI COMPLEX WITH 0.1% AVAILABLE $I_2$ 1.38 g Polydextrose Iodine
30./00 g Glycerin
00.25 g Alipal CO-436
0.056 Buffer
Water to 100 cc.

PVPI COMPLEX WITH 2.0% AVAILABLE $I_2$ 20.0 g PVPI
30.0 g Glycerin
0.25 g Alipal CO-436
4.18 g Buffer
Water to 100 cc.

PVPI COMPLEX WITH 1% AVAILABLE $I_2$ 10.31 g PVPI
30.0 g Glycerin
0.25 g Alipal CO-436
2.09 g Buffer
Water to 100 cc.

PVPI COMPLEX WITH 0.25% AVAILABLE $I_2$ 2.58 g PVPI
30.0 g Glycerin
0.25 g Alipal CO-436
0.523 g Buffer
Water to 100 cc.

PVPI COMPLES WITH 0.1% AVAILABLE $I_2$ 1.031 g PVPI
30.0 g Glycerin
00.25 g Alipal CO-436
0.209 g Buffer
Water to 100cc.

The results of the tests conducted as set forth in the following tables:

TABLE 2

Comparison of Polydextrose Iodine Complex with Polyvinylpyrrolidone Iodine Complex with regards to Killing Time
*S. aureus* #1, Penicillin Sensitive

|  | 15 sec. | 30 sec. | 1 min. | (1 min.) D-10 value | Result |
|---|---|---|---|---|---|
| *PDI Complex 2.0% Av. $I_2$ | <10 | <10 | <10 | <15 | complete kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | slower kill |
| **PVPI Complex 2.0% Av. $I_2$ | 7. × 10³ (3.85) | 3.0 × 10⁴ (4.48) | 3.4 × 10⁴ (4.53) | 97 sec | slower kill |
| PVPI Complex 1.0% Av. $I_2$ | <10 | <10 | <10 | <15 | complete kill |
| PVPI Complex 0.25% Av. $I_2$ | <10 | <10 | <10 | <15 | complete kill |
| PVPI Complex 0.1% Av. $I_2$ | <10 | <10 | <10 | <15 | complete kill |
| PDI Complex 2.0% Av. $I_2$ | 1.2 × 10³ (3.08) | 8.9 × 10² (2.95) | 1.1 × 10³ (3.04) | 28 sec. | slow kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | complete kill |
| PVPI Complex 2.01% Av. $I_2$ | <10 | <10 | <10 | <15 | complete kill |
| PVPI Complex 1.1% Av. $I_2$ | 360 (2.56) | 210 (2.32) | 160 (2.20) | 20 sec | slower kill |
| PVPI Complex 0.25% Av. $I_2$ | <10 | <10 | <10 | <15 | complete kill |
| PVPI Complex 0.1% Av. $I_2$ | <10 | <10 | <10 | <15 | complete kill |

MATCHED PAIR ANALYSIS

| | | | |
|---|---|---|---|
| (A) | PDI Complex 2.0% Av. $I_2$ | > | PVPI Complex 2.0% Av. $I_2$ |
| (B) | PDI Complex 1.0% Av. $I_2$ | = | PVPI Complex 1.0% Av. $I_2$ |
| (C) | PDI Complex 0.25% Av. $I_2$ | = | PVPI Complex 0.25% Av. $I_2$ |
| (D) | PDI Complex 0.1% Av. $I_2$ | = | PVPI Complex 0.1% Av. $I_2$ |
| (E) | PDI Complex 2.0% Av. $I_2$ | < | PVPI Complex 2.0% Av. $I_2$ |
| (F) | PDI Complex 1.0% Av. $I_2$ | > | PVPI Complex 1.0% Av. $I_2$ |
| (G) | PDI Complex 0.25% Av. $I_2$ | = | PVPI Complex 0.25% Av. $I_2$ |
| (H) | PDI Complex 0.1% Av. $I_2$ | = | PVPI Complex 0.1% Av. $I_2$ |

CONCLUSION:
1. In samples killed rapidly with $D_{10}$-values

TABLE 2-continued

|   | in most cases being <15 seconds, except for: | |
|---|---|---|
| 2. | PVPI Complex 2.0% Av. $I_2$ | slower kill |
|   | PDI Complex 2.0 Av. $I_2$ | relatively |
|   | PVPI Complex 1.0% Av. $I_2$ | |
| 3. | PVPI Complex 2.0% Av. $I_2$ | was least active |

*POLYDEXTROSE IODINE COMPLEX
**Polyvinyl pyrrolidone Iodine Complex

TABLE 2

Comparison of Polydextrose - Iodine Complex
with Polyvinylpyrrolidone - Iodine complex with regard to killing time
*S. aureus* #4, Penicillin Resistant

|   | 15 sec. | 30 sec. | 1 min. | value | result |
|---|---|---|---|---|---|
| PDI Complex 2.0% Av. $I_2$ | <10 | <10 | <10 | <15 | complete kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | complete kill |
| PVPI Complex 2.0% Av. $I_2$ | $1.0 \times 10^5$ (5.0) | $1.8 \times 10^4$ (4.26) | $6.0 \times 10^3$ (3.78) | 46 sec. | slower kill |
| PVPI Complex 1.0% Av. $I_2$ | <10 | <10 | <10 | <15 | complete kill |
| PVPI Complex 0.25% Av. $I_2$ | <10 | <10 | <10 | <15 | complete kill |
| PVPI Complex 0.1% Av. $I_2$ | <10 | <10 | <10 | <15 | complete kill |
| PDI Complex 2.0% Av. $I_2$ | 730 (2.86) | 730 (2.86) | 530 (2.72) | 25 sec. | slower kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | complete kill |
| PVPI Complex 2.0% Av. $I_2$ | $6.0 \times 10^4$ (3.78) | 50 (1.70) | <10 | 12 sec. | complete kill |
| PVPI Complex 1.0% Av. $I_2$ | 550 (2.74) | 260 (2.41) | 330 (2.52) | 23 sec. | slower kill |
| PVPI Complex 0.25% Av. $I_2$ | $2.9 \times 10^4$ (4.46) | 150 (2.18) | 10 | 24 sec. | slower kill |
| PVPI Complex 0.1% Av. $I_2$ | <10 | <10 | <10 | <15 | complete kill |

MATCHED PAIR ANALYSIS

| (A) | PDI Complex 2.0% Av. $I_2$ | > | PVPI Complex 2.0% Av. $I_2$ |
|---|---|---|---|
| (B) | PDI Complex 1.0% Av. $I_2$ | = | PVPI Complex 1.0% Av. $I_2$ |
| (C) | PDI Complex 0.25% Av. $I_2$ | = | PVPI Complex 0.25% Av. $I_2$ |
| (D) | PDI Complex 0.1% Av. $I_2$ | = | PVPI Complex 0.1% Av. $I_2$ |
| (E) | PDI Complex 2.0% Av. $I_2$ | < | PVPI Complex 2.0% Av. $I_2$ |
| (F) | PDI Complex 1.0% Av. $I_2$ | > | PVPI Complex 1.0% Av. $I_2$ |
| (G) | PDI Complex 0.25% Av. $I_2$ | = | PVPI Complex 0.25% Av. $I_2$ |
| (H) | PDI Complex 0.1% Av. $I_2$ | = | PVPI Complex 0.1% Av. $I_2$ |

CONCLUSION:

| 1. | In samples killed rapidly with $D_{10}$-values in most cases being <15 seconds, except for: | |
|---|---|---|
| 2. | PVPI Complex 2.0% Av. $I_2$ | slower kill |
|   | PDI Complex 2.0% Av. $I_2$ | relatively |
|   | PVPI Complex 1.0% Av. $I_2$ | |
| 3. | PVPI Complex 2.0% Av. $I_2$ | was least active |

TABLE 3

Comparison of Polydextrose - Iodine Complex with
Polyvinylpyrrolidone - Iodine Complex with regard to killing time
*S. aureus* #30 Toxic Shock Strain

|   | 15 sec. | 30 sec. | 1 min. | (1 min.) D-10 value | Result |
|---|---|---|---|---|---|
| PDI Complex 2.0% Av. $I_2$ | <10 | <10 | <10 | <15 | complete kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | complete kill |
| PVPI Complex 2.0% Av. $I_2$ | $1.0 \times 10^5$ (5.0) | $5.0 \times 10^4$ (4.70) | $4.3 \times 10^4$ (4.63) | 49 sec. | slower kill |
| PVPI Complex 1.0% Av. $I_2$ | <10 | <10 | <10 | <15 | complete kill |
| PVPI Complex 0.25% Av. $I_2$ | 30 (1.48) | <10 | <10 | 3 sec. | complete kill |
| PVPI Complex 0.1% Av. $I_2$ | 190 (2.28) | <10 | <10 | 49 sec. | complete kill |
| PDI Complex 2.0% Av. $I_2$ | 880 (2.94) | 740 (2.87) | 540 (2.73) | 19 sec. | slower kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | complete kill |
| PVPI Complex 2.0% Av. $I_2$ | $7.0 \times 10^4$ (4.85) | $6.1 \times 10^2$ (2.79) | $1.3 \times 10^2$ (2.11) | 16 sec. | slower kill |
| PVPI Complex 1.0% Av. $I_2$ | $4.9 \times 10^4$ | 290 | 320 | 18 sec. | slower kill |

TABLE 3-continued

| | 15 sec. | 30 sec. | 1 min. | (1 min.) D-10 value | Result |
|---|---|---|---|---|---|
| | (4.69) | (2.46) | (2.51) | | |
| PVPI Complex 0.25% Av. $I_2$ | $8.5 \times 10^3$ | <10 | <10 | 8 sec. | slower kill |

MATCHED PAIR ANALYSIS

| | | | | |
|---|---|---|---|---|
| (A) | PDI Complex 2.0% Av. $I_2$ | > | PVPI Complex 2.0% Av. $I_2$ |
| (B) | PDI Complex 1.0% Av. $I_2$ | = | PVPI Complex 1.0% Av. $I_2$ |
| (C) | PDI Complex 0.25% Av. $I_2$ | > | PVPI Complex 0.25% Av. $I_2$ |
| (D) | PDI Complex 0.1% Av. $I_2$ | > | PVPI Complex 0.1% Av. $I_2$ |
| (E) | PDI Complex 2.0% Av. $I_2$ | = | PVPI Complex 2.0% Av. $I_2$ |
| (F) | PDI Complex 1.0% Av. $I_2$ | > | PVPI Complex 1.0% Av. $I_2$ |
| (G) | PDI Complex 0.25% Av. $I_2$ | > | PVPI Complex 0.25% Av. $I_2$ |
| (H) | PDI Complex 0.1% Av. $I_2$ | > | PVPI Complex 0.1% Av. $I_2$ |

CONCLUSION:

1. In samples killed rapidly with $D_{10}$-values in most cases being <15 seconds, except for:
2. PVPI Complex 2.0% Av. $I_2$ — slower kill
   PDI Complex 2.0% Av. $I_2$ — relatively
   PVPI Complex 2.0% Av. $I_2$
   PVPI Complex 1.0% Av. $I_2$
   PVPI Complex 0.25% Av. $I_2$
   PVPI Complex 0.1% Av. $I_2$
3. PVPI Complex 2.0% Av. $I_2$ — was least active

TABLE 4

Comparison of Polydextrose - Iodine Complex with Polyvinylpyrrolidone - Iodine Complex with regard to killing time
*S. epidermidis* Normal Skin Flora

| | 15 sec. | 30 sec. | 1 min. | (1 min.) D-10 value | Result |
|---|---|---|---|---|---|
| PDI Complex 2.0% Av. $I_2$ | <10 | <10 | <10 | <15 | complete kill |
| PDI Complex 1.0% Av. $I_2$ | <10 | <10 | <10 | <15 | complete kill |
| PDI Complex 0.25% Av. $I_2$ | $8.3 \times 10^3$ (3.92) | <10 | <10 | <13 | complete kill |
| PDI Complex 0.1% Av. $I_2$ | <10 | <10 | <10 | <15 | complete kill |
| PVPI Complex 2.0% Av. $I_2$ | $3.5 \times 10^3$ (3.54) | $3.4 \times 10^3$ (3.53) | $6.7 \times 10^2$ (2.82) | 27 sec. | slower kill |
| PVPI Complex 1.0% Av. $I_2$ | <10 | <10 | <10 | <15 | complete kill |
| PVPI Complex 0.25% Av. $I_2$ | 140 (2.15) | <10 | <10 | <15 | complete kill |
| PVPI Complex 0.1% Av. $I_2$ | <10 | <10 | <10 | <15 | complete kill |
| PDI Complex 2.0% Av. $I_2$ | 440 (2.64) | 400 (2.60) | 490 (2.69) | 26 sec. | slower kill |
| PDI Complex 1.0% Av. $I_2$ | <10 | <10 | <10 | <15 | complete kill |
| PDI Complex 0.25% Av. $I_2$ | <10 | <10 | <10 | <15 | complete kill |
| PDI Complex 0.1% Av. $I_2$ | <10 | <10 | <10 | <15 | complete kill |
| PDI Complex 2.0% Av. $I_2$ | 200 | <10 | <10 | 5 sec. | complete kill |
| PVPI Complex 1.0% Av. $I_2$ | 410 | <10 | <10 | 6 sec. | complete kill |
| PVPI Complex 0.25% Av. $I_2$ | $1.1 \times 10^3$ | <10 | <10 | 6 sec. | complete kill |
| PVPI Complex 0.1% Av. $I_2$ | <10 | <10 | <10 | 8 sec. | slower kill |

MATCHED PAIR ANALYSIS

| | | | | |
|---|---|---|---|---|
| (A) | PDI Complex 2.0% Av. $I_2$ | > | PVPI Complex 2.0% Av. $I_2$ |
| (B) | PDI Complex 1.0% Av. $I_2$ | = | PVPI Complex 1.0% Av. $I_2$ |
| (C) | PDI Complex 0.25% Av. $I_2$ | < | PVPI Complex 0.25% Av. $I_2$ |
| (D) | PDI Complex 0.1% Av. $I_2$ | = | PVPI Complex 0.1% Av. $I_2$ |
| (E) | PDI Complex 2.0% Av. $I_2$ | < | PVPI Complex 2.0% Av. $I_2$ |
| (F) | PDI Complex 1.0% Av. $I_2$ | > | PVPI Complex 1.0% Av. $I_2$ |
| (G) | PDI Complex 0.25% Av. $I_2$ | > | PVPI Complex 0.25% Av. $I_2$ |
| (H) | PDI Complex 0.1% Av. $I_2$ | = | PVPI Complex 0.1% Av. $I_2$ |

CONCLUSION:

1. In samples killed rapidly with $D_{10}$-values in most cases being <15 seconds, except for:
2. PVPI Complex 2.0% Av. $I_2$ — slower kill
   PDI Complex 2.0% Av. $I_2$ — relatively

TABLE 5

Comparison of Polydextrose - Iodine complex with Polypyrrolidone - Iodine complex with regards to killing time
Dry Formulations, Staphylococcicidal Activity
Rankings of Activity

| | $D_{10}$-value (in seconds to kill 1-log) | | | calc. at 15 or 60 sec. |
|---|---|---|---|---|
| | S. aureus #1 | S. aureus #4 | S. aureus #30 | S. epid. |
| PDI Complex 2.0% Av. $I_2$ | <15 | <15 | <15 | <15 |
| PDI Complex 1.0% Av. $I_2$ | <15 | <15 | <15 | <15 |
| PDI Complex 0.25% Av. $I_2$ | <15 | <15 | <15 | 13 |

TABLE 5-continued

| | | | | |
|---|---|---|---|---|
| PDI Complex 0.1% Av. $I_2$ | <15 | <15 | <15 | <15 |
| PVPI Complex 2.0% Av. $I_2$ | 97 | 46 | 49 | 27 |
| PVPI Complex 1.0% Av. $I_2$ | <15 | <15 | <15 | <15 |
| PVPI Complex 0.25% Av. $I_2$ | <15 | <15 | 3 | <15 |
| PVPI Complex 0.1% Av. $I_2$ | <15 | <15 | 4 | <15 |
| PDI Complex 2.0% Av. $I_2$ | 28 | 25 | 19 | 26 |
| PDI Complex 1.0% Av. $I_2$ | <15 | <15 | <15 | <15 |
| PDI Complex 0.25% Av. $I_2$ | <15 | <15 | <15 | <15 |
| PDI Complex 0.1% Av. $I_2$ | <15 | <15 | <15 | <15 |
| PVP Complex 2.0% Av. $I_2$ | <15 | 12 | 16 | 5 |
| PVP Complex 1.0% Av. $I_2$ | 20 | 23 | 18 | 6 |
| PVP Complex 0.25% Av. $I_2$ | <15 | 24 | 8 | 8 |
| PVP Complex 0.1% Av. $I_2$ | <15 | <15 | 6 | <15 |
| 15 seconds incomplete kill | (a) 3/16 | (b) 5/16 | (c) 8/16 | (d) 6/16 |

LABORATORY REPORT

NOTE: <15 seconds indicates no colonies counted at the $10^{-1}$ dilution at 15 seconds exposure and, thus, a count of <10 survivors/ml Such a value could be as low as 1 second (i.e. <15 sec = complete kill for this test sensitivity limits) a. *S. aureus* #1 was the most sensitive strain with only 3/16 showing incomplete kill at 15 sec. b. 5/6 d. 6/16 c. *S. aureus* (toxic shock) was the most resistant strain in this series with as many as 8/16 with survivors at 15 seconds.

OVER-ALL CONCLUSIONS

1. Matched Pair Analyses show differences and equivalences, as seen in tables 1-4.
2. PDI Complex 0.1% Av. $I_2$ was the least active. PVPI 2.0% Av. $I_2$
3. PDI Complex 2.0% Av. $I_2$  
   PVPI Complex 2.0% Av. $I_2$  
   PVPI Complex 1.0% Av. $I_2$  
   PVPI Complex 0.25% Av. $I_2$  
   } also showed diminished 15 second kills.

TABLE 6

Comparison of Polydextrose - Iodine Complex with Polyvinylpyrrolidone - Iodine complex with regard to killing time
*B. pumilus* spores
GBL no. 24760/15-30

| | 1 hr. | 3 hrs | 6 hrs. | 24 hrs | $D_{10}$ |
|---|---|---|---|---|---|
| PDI Complex 2.0% Av. $I_2$ | 850 | 10 | <10 | <10 | |
| PDI Complex 1.0% Av. $I_2$ | $1.2 \times 10^3$ | <10 | <10 | <10 | |
| PDI Complex 0.25% Av. $I_2$ | 100 | <10 | <10 | <10 | |
| PDI Complex 0.1% Av. $I_2$ | 950 | <10 | <10 | <10 | |
| PVPI Complex 2.0% Av. $I_2$ | $6.8 \times 10^5$ | $9.6 \times 10^5$ | $4.2 \times 10^5$ | $2.6 \times 10^4$ | inactive |
| PVPI Complex 1.0% Av. $I_2$ | $1.4 \times 10^5$ | $9.1 \times 10^4$ | $1.2 \times 10^4$ | $7.0 \times 10^3$ | inactive |
| PVPI Complex 0.25% Av. $I_2$ | $8.6 \times 10^4$ | $1.1 \times 10^3$ | $1.4 \times 10^4$ | 660 | |
| PVPI Complex 0.1% Av. $I_2$ | $1.6 \times 10^6$ | $4.9 \times 10^5$ | $8.3 \times 10^4$ | 50 | |
| PDI Complex 2.0% Av. $I_2$ | 10 | <10 | <10 | <10 | |
| PDI Complex 1.0% Av. $I_2$ | <10 | <10 | <10 | <10 | |
| PDI Complex 0.25% Av. $I_2$ | <10 | <10 | <10 | <10 | |
| PDI Complex 0.1% Av. $I_2$ | 120 | <10 | <10 | <10 | |
| PVP Complex 2.0% Av. $I_2$ | $7.9 \times 10^5$ | $6.2 \times 10^5$ | $1.6 \times 10^4$ | 240 | |
| PVP Complex 1.0% Av. $I_2$ | $8.0 \times 10^5$ | $1.7 \times 10^5$ | $7.0 \times 10^3$ | 30 | |
| PVP Complex 0.25% Av. $I_2$ | $3.5 \times 10^5$ | $6.3 \times 10^4$ | $7.3 \times 10^2$ | <10 | |
| PVP Complex 0.1% Av. $I_2$ | $1.7 \times 10^5$ | $8.9 \times 10^4$ | 70 | <10 | |

Paired Rankings

| | | | |
|---|---|---|---|
| (A) | PDI Complex 2.0% Av. $I_2$ | > | PVPI Complex 2.0% Av. $I_2$ |
| (B) | PDI Complex 1.0% Av. $I_2$ | > | PVPI Complex 1.0% Av. $I_2$ |
| (C) | PDI Complex 0.25% Av. $I_2$ | > | PVPI Complex 0.25% Av. $I_2$ |
| (D) | PDI Complex 0.1% Av. $I_2$ | > | PVPI Complex 0.1% Av. $I_2$ |
| (E) | PDI Complex 2.0% Av. $I_2$ | > | PVPI Complex 2.0% Av. $I_2$ |
| (F) | PDI Complex 1.0% Av. $I_2$ | > | PVPI Complex 1.0% Av. $I_2$ |
| (G) | PDI Complex 0.25% Av. $I_2$ | > | PVPI Complex 0.25% Av. $I_2$ |
| (H) | PDI Complex 0.1% Av. $I_2$ | > | PVPI Complex 0.1% Av. $I_2$ |

BEST FORMULATIONS FOR ALL COCCI AND SPORES

PDI COmplex 1.0% Av. $I_2$
PDI Complex 0.25% Av. $I_2$

According to the results of the test conducted as outlined above, the polydextrose iodine complexes (PDI) with 2%, 1%, 0.25%, and 0.1% available iodine content, were found to be more potent than the polyvinylpyrrolidone iodine (PVPI) complexes having the same respective percentages of available iodine content. The polydextrose iodine complexes having only the buffer with 1% and 0.2% available iodine content, were found to be the best formulations for all cocci and spores, whereas the polyvinylpyrrolidone iodine formulations with 2% available iodine, were found to be the least active. Thus it is quite clear that the polydextrose iodine iodophor complexes of the present invention provide distinct antibacterial and germicidal benefits, with improved performance over the previously-used polyvinylpyrrolidone iodine (PVPI) iodophor complexes.

The viscosity of a polydextrose-iodine (PDI) iodophor complex has also been analyzed, as opposed to viscosity of just polydextrose solutions alone. PDI iodophor solutions have been prepared containing respective amounts of 50% weight/volume, 40% weight/volume, 30% weight/volume, 20% weight/volume, 8% weight/volume, 5% weight/volume, and 1% weight/volume of iodine therein. These respective solutions are filtered through 0.45 micron filters. Relative viscosities are measured using Ubbelohde glass capillary viscometers, with size 0 B for 50-20% solutions, and size 0 C for 10-1% solutions. The relative viscosity at 25° C.±0.05° C., is measured as a ratio of flow times for the sample solutions, over the flow time of pure water.

The moisture content of the polydextrose-iodine (PDI) complex is determined by the Karl-Fischer titration method, to be 11.28%. Available iodine has been determined to be 7.45% and the iodide concentration has been determined as 6.745% KI. The overall content of polydextrose and the polydextrose-iodine complex (PDI) is therefore 74.52% by weight.

The viscosities of the respective polydextrose-iodine complexes, and the polydextrose control, were determined. It was found that polydextrose-iodine complexes exhibit a higher degree of viscosity than solutions of polydextrose alone, at equivalent polydextrose concentrations. The resulting estimate of intrinsic viscosity, (n), is also greater for polydextrose-iodine complexes, than for polydextrose solutions alone. This indicates that the polydextrose molecule is slightly expanded when in solution of the polydextrose-iodine complexes, as would be expected with inclusion of iodine or iodide in the formation of the requisite polymer matrix in the iodophor.

The specific resistance or equivalent conductance of the PDI iodophores, has also been compared with the PVP-I iodophores. Specific electrical resistance of a solution is defined as conductance per unit cross-sectional area per centimeter.

For analysis of the equivalent conductance, the polydextrose iodine and polyvinylpyrrolidone iodine complexes were prepared as follows, in addition to preparation of iodine solution, and iodine control solution.

The iodine solution itself was prepared by dissolving 100 g of potassium iodide (KI) in 150-200 cc of water. 50.0 g of elemental iodine, $I_2$, was added with stirring to this solution, which was then raised to 500 ml in volume, by the further addition of water. The iodine control solution was prepared by diluting 5 cc of iodine solution in a volumetric flask, followed by stirring for one hour at room temperature, and allowing the same to stand overnight.

The polydextrose-iodine complex was prepared by dissolving 10.0 g polydextrose in 70 cc of water, with 5 cc of iodine stock solution being added with stirring thereto. The solution was then raised to the volume of a 100 cc volumetric flask, by addition of water therein, followed by stirring for one hour at room temperature, and allowing the same to stand overnight.

The polyvinylpyrrolidone-iodine complex (PVP-I) was prepared by dissolving 10.0 g of PVP-K30 in 60 cc of water. 5 cc of iodine solution was dissolved in 25 cc of water, with the resulting iodine solution was slowly added to the PVP solution with rapid stirring. This solution thus formed was stirred at room temperature until all gelatinous material was dissolved, stirring being carried on for up to one-half hour. The resulting solution was raised to a volume of 100 cc, and stirred for the remainder of the hour, followed by standing overnight.

Each of the above four prepared solutions was assayed before analysis for available iodine content, using 0.02 N thiosulfate, and assayed for total iodides ($I_2$ + $I^-$), using potentiometric titration with 0.1 N silver nitrate. Similarly, solutions of PVP and polydextrose alone, containing respective amounts of 8.0 g/l polymer, were prepared by dissolving 0.8 g of respective polymer in 70 cc water, to bring the resulting solutions to the requisite volume levels as the other solutions so prepared. A 0.5 M potassium chloride (KCl) solution was also prepared at the concomitant volume.

Conductance and capacitance of each of the above seven solutions prepared, were analyzed for the various concentrations thereof, using the General Radio Capacitance Measuring Assembly. Experimental solutions of the iodine control solution, the polydextrose-iodine complex, the PVP-I complex, and solutions of PVP alone and polydextrose alone, were diluted to concentrations of 2 ml/100, 1 ml/100, 0.1 ml/50, 0.1 ml/100 for iodine containing solutions, and to concentrations of 20 ml/100, 100 ml/100, 2 ml/100, and 1 ml/100 for the polydextrose or PVP solutions alone. The parallel conductance and capacitance were read directly from the general radio capacitance measuring instrument, using a model CEL3-J-1 cell. The potassium chloride (KCl) solution was measured at concentrations of 0.01 M, 0.005 M, 0.001 M, 0.00005 M, and 0.0001 M respectively.

The tests confirmed that as the concentration of PVP in solution increases, the equivalent conductance decreases. However, if the concentration of PVP decreases, then the equivalent conductance increases exponentially. In the case of polydextrose, with an equivalent conductance of 0.018 $ohm^{-1}cm^{-3}$, as the concentration of polydextrose increases, the equivalent conductance decreases linearly. This tends to substantiate that polydextrose ionizes less than polyvinylpyrrolidone. In the case of iodine solution (Lugol's Solution), as the concentration increases, equivalent conductance decreases.

Concerning the polydextrose-iodine iodophor complex (PDI), as concentration increases, conductance decreases. However, if concentration decreases, i.e. is diluted, conductance increases linearly. This substantiates that the degree of binding remains substantially constant with dilution of PDI complexes, due to the binding of tri-iodide and/or iodide to the polydextrose. The contribution of equivalent conductance by the polydextrose is about 10% at zero concentration. The equivalent conductance for PDI is 160.4 $ohm^{-1}cm^{-3}$. This is far lower than the equivalent conductance for PVPI (216.8 $ohm^{-1}cm^{-3}$), and also for the equivalent conductance of the iodine solution (222.7 $ohm^{-1}cm^{-3}$). This tends to confirm the binding of $I^{-3}$ and/or $I^-$ to the polydextrose in the PDI iodophors. The higher the equivalent conductance number in the PDI iodophor, the higher the free ion concentration and the less binding to the polydextrose polymer.

In the case of PVP iodophor, the data substantiates that there is some binding of $I^{-3}$ and/or $I^-$ to the PVP, but less than in the PDI iodophor. There is no binding occurring at all in the iodine solution itself, since the iodine is completely ionized in solution. In the PVPI complex, the equivalent conductance bears a linear relationship to the square root of the total ion concentration, the equivalent conductance increasing with concentration.

Relative to the iodine solution, polydextrose iodine complex (PDI) exhibits a much lower value of equivalent conductance, and the additivity rule does not hold in this instance in the range of zero concentration. Neglecting the contribution of polydextrose to the conductivity, since it is negligible, the decrease in zero concentration equivalent conductivity must be due to a decrease in the free ion concentration, implying complexing of ions by the polydextrose. However, a reversible equilibrium does not give rise to a linear curve in the square root of total ion concentration, and in the rate of zero concentration, the equivalent conductivity of PDI should approach that of iodine solution alone, as the equilibrium shifts towards complete dissociation. This implies a "irreversible" binding process (no covalent interation occurs because titration assays exhibit no loss of ions by chemical interaction).

Concerning the polyvinylpyrrolidone-iodine complex, PVP itself exhibits some loss of total ions, but no loss of available iodine, indicating the possibility of a small degree of covalent interaction with the iodine. However, the zero concentration equivalent conductivity is only slightly less than that for iodine solution alone, indicating little or no binding of $I^-$ or $I^-_3$ by the PVP.

Therefore, it is quite clearly observed that on the basis of this data noted above, polydextrose is definitely complexed with tri-iodide ($I^{-3}$) and/or iodide ($I^-$), because the equivalent conductance at zero concentration is significantly less than that for iodine solution alone (e.g., Lugol's Solution). The ratio of free ions to bound ions in PDI is constant, even as the concentration decreases. Thus, PDI exhibits lower free ion concentration than iodine solution. This is possibly due to the hydrogen bonding or osmotic equilibrium that is involved. The lower equivalent conductance of PDI tends to indicate bonding $I^{-3}$ and/or $I^-$ to the polydextrose.

Regarding PVPI, it is possible that the iodine may be enclosed in the helical polymer matrix. This data seems to confirm that there is not much binding of $I^{-3}$ and/or $I^-$ to the PVP. It appears that contribution by PVP to equivalent conductance of polyvinylpyrrolidone-iodine, is about ten times greater than the contribution of polydextrose to the PDI complex.

Absorbance tests indicate complexing of the iodine by the polydextrose and polyvinylpyrrolidone. The rate of release of iodine from polydextrose iodine iodophor is intermediate between the rate of release for polyvinylpyrrolidone iodine and for just iodine solution alone. In other words, the results show a decreasing rate of release from iodine solution, to polydextrose iodine, to polyvinylpyrrolidone iodine.

Equilibrium iodine concentration was determined for the polydextrose-iodine iodophor complexes having the respective concentrations of 7.45% and 3.25% available iodine, with these equilibrium iodine determinations being compared with values obtained for the polyvinylpyrrolidone iodine (PVP-I) complex having 9.6% available iodine, and for the iodine solution alone. The amount of solution containing 1.0 g. iodine was calculated for each of these respective solutions. Then, this amount of solution from each of the respective solutions noted above, was dissolved in 80 ml. water, with water being added to raise the volume thereof to 100 ml in a 100 ml volumetric flask. The resulting solution from each of the respective compositions was then used to determine the equilibrium iodine concentration. For each of the four samples so prepared, four ratios of aqueous solution to heptane were used for the extractions that were carried out: 3 aqueous:1 heptane, 2 aqueous:1 heptane, 1 aqueous:1 heptane, and 0.5 aqueous:1 heptane. The aqueous solution and heptane were pipetted into a 20 ml. centrifuge tube, shaken for one minute, and then centrifuged at 2,000 rpm for 2 minutes. Ambient temperature was noted.

Then, absorbance of iodine into the organic heptane layer at 522.6 nm was measured and converted into ppm iodine in the aqueous phase according to the following formula:

ppm $I_2$ (heptane phase) = mg. $I_2$ STD./absorbance $I_2$ (absorbance in sample) × 10 ppm $I_2$ (aqueous phase) = ppm $I_2$ (heptane)/$K_p$ $K_p$ (at 23° C.) = 45.0 = solubility of $I_2$ in heptane at 23° C./0.03 g/ml $I_2$ in water The calculations were made for each of the four samples so prepared with the heptane and the results being plotted on a graph. The results as determined from the extraction were as follows:

| | Equilibrium Iodine |
|---|---|
| PDI, 7.45% Available $I_2$ | 103.3 ppm |
| Iodine Solution Alone | 141.7 ppm |
| PVP-I Complex | 1.01 ppm |

The data clearly confirms that the amount of equilibrium iodine released from polydextrose iodine iodophor (PDI) is far less than from iodine solution, due to the complexing of iodine with the polydextrose. When compared with the well-know PVPI iodophor, the amount of equilibrium iodine released from PDI is far greater than from PVPI, thus providing a greater germicidal and antiseptic effect.

The percent of available iodine in an aqueous polydextrose iodine antiseptic iodophor composition, may vary from 0.01% to 20% based on the overall weight of the particular composition or solution.

The ultraviolet/visual absorbance scan of the polydextrose iodine complex having 7.45% available iodine content, was determined and compared with the scan for polydextrose solution alone. An aqueous solution of the polydextrose-iodine complex noted above was prepared to contain 0.004% available iodine by weight/volume of solution. An ultraviolet/visual absorbance scan from 600-190 nm was taken. Similarly, a solution of polydextrose was prepared to contain an approximate equivalent concentration of polydextrose alone (0.06% polydextrose weight/volume of solution). An ultraviolet/visual scan from 600 nm-190 nm was also taken for this polydextrose solution alone.

The results were as follows:

| | Peak Maxima |
|---|---|
| PDI | 351.5 nm, 287.5 nm, 223 nm, 209 nm |
| Polydextrose Solution Alone | 281 nm, 192 nm, shoulder at 221 nm |

These results demonstrate a significant difference between the PDI complex and the polydextrose solution alone, especially in the absence of absorbance peaks at 351 nm and 209 nm for the polydextrose solutions alone.

There is the presence of absorbant peaks at 351 nm and 209 nm in PDI solution, whereas there is none in the corresponding polydextrose solution alone. At the same time, the PDI solution shows no absorbance at 192 nm, a strong absorbance at 287.5 nm, and a strong absorbance at 223 nm, as opposed to a weak absorbance at 281 nm and a weak shoulder at 221 nm for the polydextrose solution alone. The peaks occurring in the PDI solution at 351.5 nm and 223 nm correspond to the absorbance of $I_3^-$ and $I^-$ respectively, indicating the presence of tri-iodide and iodide ions within the PDI complex.

The infrared spectra of the respective polydextrose-iodine complexes having 7.45% available iodine and 3.25% available iodine respective, were taken using a potassium bromide (KBr) pellet. Scans were taken over the range of 4,000 $cm^{-1}$ to 200 $cm^{-1}$. Both scans were extremely similar to the infrared scan of polydextrose solution alone. Slight differences occurred in the region of 1,500 $cm^{-1}$ to 1,200 $cm^{-1}$. A very slight shoulder appears in the PDI scans, while increased intensity of the peak at 800 to 300 $cm^{-1}$ has been observed.

The present invention will be explained in further detail by way of the following specific examples, which are not to be construed as limiting the scope of the present invention in any way.

EXAMPLE 1

25 ml of iodine solution containing 629.2 mg $I_2$/ml (total amount of iodine present in the solution equal to 15.73 g) was freeze dried, with the weight of the freeze-dried sample being determined as 10.3 g. The total amount of iodine found in the sample was 0.123 g, with a loss of iodine equal to 99.3%. When this iodine solution was reacted with polydextrose polymer solution followed by freeze drying, the loss of iodine is low. This demonstrates that the polydextrose polymer forms a complex with the iodine or tri-iodide ion since in the absence of polydextrose, the percent of iodine loss is 99.3% from the iodine solution.

EXAMPLE 2

0.7 g of pulverized, resublimed iodine is added portionwise to 70 cc of a 5% polydextrose solution, with constant stirring at 35° C. The resultant solution is heated to 65° C., with the temperature being maintained for 2 hours. The solution is then allowed to cool to room temperature overnight, filtered, and freeze dried to a fine powder. The available iodine in this preparation was assayed at 0.01%.

EXAMPLE 3

3.5 g of pulverized, resublimed iodine was added at 40° C. to 200 cc of a 10% polydextrose solution, with stirring. The mixture was heated slowly to 75° C., maintained for 4 hours at this temperature, and then allowed to cool, followed by filtering and freeze-drying. The available iodine content of the resulting preparation was assayed at 0.14%.

EXAMPLE 4

5.25 g of pulverized, resublimed iodine was added at 40° C. to 200 cc of a 15% polydextrose solution in water, with stirring. The resulting mixture was heated to 70° C., with a temperature being maintained for 4 hours. The reaction solution was then cooled over an ice bath, filtered, and freeze-dried to a fine powder. Available iodine content was determined as 0.48%.

EXAMPLE 5

6.5 g of pulverized, resublimed iodine was added to 200 cc of a 60% polydextrose solution, with stirring. The mixture was then heated with stirring for 4 hours at 75° C. Then, the resulting composition was allowed to cool to room temperature, filtered, and freeze-dried. Available iodine content was assayed as 0.93%.

EXAMPLE 6

6.5 g of resublimed iodine was added to 200 cc of a 60% polydextrose solution in water, at 40° C. with stirring. After completion of the addition of iodine, ten drops of 47–51% hydriodic acid was added. The mixture was then heated to 75° C., with the temperature being maintained for 4 hours. The resulting solution was cooled and filtered, with the available iodine content thereof determined as 1.026%.

EXAMPLE 7

6.5 g of resublimed iodine was added with stirring at room temperature to 100 cc of 60% polydextrose solution in water. Ten drops of hydriodic acid was then added to the solution. The mixture was then stirred at room temperature for one hour, filtered an freeze-dried. Available iodine content was determined as 0.22%.

EXAMPLE 8

3.25 g of resublimed iodine was added with stirring to 100 cc of a 60% polydextrose solution. After completion of the iodine addition, 10 drops of hydriodic acid was added. The mixture was then stirred at room temperature for 1 hour, then filtered and freeze-dried, with available iodine content determined as 0.29%.

EXAMPLE 9

3.25 g of resublimed iodine and 10 drops hydriodic acid were simultaneously added at room temperature to 100 cc of a 60% polydextrose solution in water, with concomitant stirring. The resulting mixture was then heated to 75° C., and the temperature maintained for 1 hour thereat. The mixture was then cooled to room temperature and filtered. The available iodine content of the resulting composition was determined at 0.7%.

EXAMPLE 10

20 g of polydextrose was added to 100 cc of water. 4.44 cc of iodine solution containing 1.8 g potential iodide and 3.2 g iodine was then added to the resulting clear polydextrose solution. After the addition of the iodine solution thereto, the resulting mixture was stirred for 1 hour at room temperature, then filtered and freeze-dried to a fine powder. Available iodine content was determined as 8.9%.

EXAMPLE 11

20 g polydextrose was dissolved in 100 cc of water at room temperature, with stirring. 2.55 cc of iodine solution, prepared as in Example 10, was then added to the stirred solution. The resulting mixture was then subsequently stirred for one hour and filtered, with available iodine content thereof determined as 5.2%.

EXAMPLE 12

400 g polydextrose was dissolved in 2,000 cc water with stirring at room temperature. 83.63 cc iodine solution prepared as in Example 10, was then added with stirring. The resulting mixture was heated to 65° C., with the temperature being maintained for one hour. The resulting solution was then cooled and spray-dried, with available iodine content as 0.05%.

EXAMPLE 13

20 g polydextrose was dissolved in 100 cc of water at room temperature with stirring. 1.07 cc of iodine solution prepared as in Example 10 was then added to the solution, followed by stirring for 1 hour. The solution was filtered, with available iodine content determined as 2.01%.

EXAMPLE 14

1.6 cc of iodine solution prepared as in Example 10 was added dropwise with stirring to 100 cc of a 20% polydextrose solution in water. The resulting solution was stirred for one hour at room temperature and filtered. The available iodine content thereof was determined as 3.2%.

EXAMPLE 15

2.01 cc of iodine solution prepared as in Example 10 was added with stirring to 100 cc of a 20% polydextrose solution in water. The solution was stirred for 1 hour at room temperature and then filtered, with available iodine determined as 4.03%.

EXAMPLE 16

3.52 cc iodine solution prepared as in Example 10 was added dropwise with stirring to 100 cc of a 20% polydextrose solution in water. The solution was stirred for 1 hour at room temperature and then filtered, with available iodine content determined as 7.01%.

EXAMPLE 17

2.69 cc of iodine solution prepared as in Example 9 was added with stirring to 100 cc of a 20% polydextrose solution in water. The resulting solution was heated to 55° C., with the temperature being maintained thereat for 1 hour. The resulting heated solution was then cooled and filtered, with available iodine content determined as 5.1%.

EXAMPLE 18

20 g of polydextrose was dissolved in 100 cc of water at room temperature. 4.54 cc of iodine solution prepared as in Example 8, was then added with stirring. The solution was heated to 55° C., with the temperature being maintained for 1 hour. The available iodine content was determined as 7.25%.

EXAMPLE 19

20 g of polydextrose was dissolved in 100 cc of water at room temperature. 0.4 cc of iodine solution was then added with stirring, followed by heating to 55° C. and maintainance with the temperature thereat for 1 hour. Cooling and filtering followed, with the available iodine content assayed at 1.06%.

EXAMPLE 20

600 g of polydextrose was dissolved in 3,000 cc of water at room temperature. 133 cc of iodine solution was then added to the polydextrose solution, followed by heating to 55° C., with the temperature being maintained for 1 hour at that level. The resulting composition was then cooled, filtered, and freeze-dried to a fine powder, with available iodine content determined as 7.19%.

EXAMPLE 21

20 g of polydextrose was dissolved in 17 cc of water at room temperature. 4.28 cc of iodine solution was then added, with the resulting mixture being heated to 55° C. The temperature was maintained for one hour, followed by cooling and filtering the solution. The solution was then freeze-dried and assayed for iodine, which yielded an available iodine content of 5.34%.

EXAMPLE 22

600 g of polydextrose was dissolved in 3,000 cc of water at room temperature. 155.0 cc of iodine solution that was prepared from 43.55 g of potassium iodide (KI) and 112.37 g. of iodine, was then added to the polydextrose solution. Subsequently, the resultant solution was heated to 55° C. with stirring, with the temperature being maintained at that level for 1 hour. The resultant solution was cooled and filtered, with the filtrate being assayed for available iodine after 6 weeks of standing at room temperature. The iodine content was found to be 8.39% after standing at room temperature for six weeks.

Aliquots of the solution prepared in this example were freeze-dried. The resulting batches were then combined and assayed for available iodine, which was found to total 7.69%.

EXAMPLE 23

20.0 g of polydextrose was dissolved in 4 cc of water at room temperature, followed by heating of the resultant solution in an oil bath at 75° C. with stirring 2.0 g of iodine was added portionwise during the stirring in the oil bath. Heating and stirring then continued for one-half hour, followed by cooling, and subsequent drying in a vacuum over phosphorous pentoxide. The weight of the dry polydextrose iodine complex was 20.5 g, with the assayed available iodine content being 0.1%.

EXAMPLE 24

40 g of polydextrose powder was dissolved in 100 cc of water, with stirring and heating at 60° C. 9.72 g of resublimed iodine was added portionwise over 15 minutes to the clear solution during the stirring and heating at 70° C. The temperature was then raised to 90°–95° C., with stirring for 30 minutes. The solution was then cooled to room temperature, and the further cooled on an ice bath, followed by filtering. The crystals were dried in a vacuum over anhydrous calcium chloride, with the assayed available iodine content found to be 0.62%.

EXAMPLE 25

One gram of resublimed iodine was dissolved in 20 cc of carbon tetrachloride ($CCl_4$). 5.0 g of polydextrose powder was added to the clear iodine solution, with stirring. The resulting suspension was stirred for 15 minutes, and then 0.3 cc of hydriodic acid (47–51% concentration) was added in dropwise fashion, over 5 minutes. The resulting suspension was then stirred for 4 hours, followed by filtering by suction. The resulting solid was partially in powder form, and was dried under vacuum over phosphorus pentoxide. The resulting weight of the solid powder was 2.9 g, with an available iodine content of 0.19%, while the weight of the gummy solid portion of the product was found to be 1.5 g, with an available iodine content of 3.8%.

EXAMPLE 26

20 g of polydextrose powder was dissolved in 100 cc of water with stirring, followed by addition of 10 cc of iodine solution to the clear polydextrose solution. The iodine solution so added was prepared from 8.2 g of potassium iodine (KI) and 13 g of iodine in 25 cc of water. The resulting iodine-polydextrose solution was stirred for half an hour, filtered, and then freeze-dried to a fine powder of the polydextrose-iodine iodophor complex. Available iodine content of this composition was determined to be 10.34%.

EXAMPLE 27

20 g of polysaccharide Ficoll polymer was dissolved in water in a 200 ml volumetric flask, and water was then added to raise the volume of the solution to 200 ml. 4 g of finely-ground iodine was then added to the solution, which was slowly heated to 95° C., with the temperature being maintained for one-half hour. The solution was then cooled to ambient temperature, filtered, and freeze-dried. The assayed iodine solid complex was determined to have 1.6% available iodine content.

EXAMPLE 28

50 g of polysaccharide Ficoll polymer was dissolved in water a 500 ml volumetric flask, with water then added to raise the volume of the solution to 500 ml. 10 g of finely-powdered iodine was then added to the solution, followed by heating for 5.5 hours at 95° C. with stirring. The solution was allowed to stand overnight, filtered, and then freeze-dried. The available iodine content thereof was assayed as 2.1%.

EXAMPLE 29

2.0 g of iodine dissolved in 75 ml of 1,2-dichloroethane, was added to 20 g of Ficoll polymer in 200 ml of 1,2-dichloroethane, with stirring. The suspension was heated to 79° C., with the temperature then being maintained for 2 hours. The resulting product was allowed to cool overnight, filtered, and freeze-dried to a fine powder. The available iodine content was assayed as 0.1%.

EXAMPLE 30

20 g of Ficoll polymer was dissolved in 100 ml of water. 4.84 ml of iodine solution was then added with stirring for 2 hours, at room temperature. The resultant liquid was assayed for available iodine, which was determined to be 9.62%.

EXAMPLE 31

7.45 ml of iodine solution prepared according to Example 10, was added to 100 ml of a 20% solution of Ficoll polymer dissolved in water, with stirring. Stirring was continued for one hour at room temperature with the solution then being assayed for available iodine. The available iodine was determined to be 14.5%.

EXAMPLE 32

7.0 ml of iodine solution was added to 100 ml of a 20% solution of Ficoll polymer in water, with stirring. The solution was then stirred for an additional hour at room temperature. The resulting solution was filtered and assayed for available iodine, which was determined to be 13.04%.

EXAMPLE 33

0.42 ml of iodine solution was added to 100 ml of a 20% solution of Ficoll polymer in water, with the resulting solution being stirred for an additional hour at room temperature. The solution was then assayed for available iodine content, which was determined to be 1.25%.

EXAMPLE 34

2.2 ml of iodine solution was added to 100 ml of a 20% solution of Ficoll polymer in water, with the resulting solution being stirred for one hour at room temperature and assayed for available iodine content. The available iodine content was determined to be 4.95%.

EXAMPLE 35

7.3 ml of iodine solution was added to 100 ml of a 20% solution of Ficoll polymer in water, followed by stirring for one hour at room temperature. The available iodine content that was assayed of this solution was 15.29%.

EXAMPLE 36

4.4 ml of iodine solution was added to 100 ml of a 20% solut of Ficoll polymer in water, with heating and stirring at 55° C. for one hour. The solution was allowed to cool to room temperature, and then filtered and assayed for iodine content. The available iodine content was determined to be 7.66%.

EXAMPLE 37

4.4 ml of iodine solution was added to 100 ml of a 20% solution of Ficoll polymer in water, with heating and stirring at 55° C. for one hour. The solution was allowed to cool, and the resulting Ficoll-iodine complex solution was assayed for available iodine content, determined to be 9.73%.

EXAMPLE 38

7.26 ml of iodine solution was added to 100 ml of a 20% solution of Ficoll polymer in water, with stirring for one hour at 55° C. The resulting Ficoll-iodine complex solution was assayed for available iodine content, determined to be 12.29%.

EXAMPLE 39

100 ml of a 20% solution of Ficoll polymer in water was heated to 45° C., with 7.3 ml of iodine solution then being added with stirring. The temperature of the resulting solution was maintained for one hour, followed by cooling. The liquid was then filtered and assayed for available iodine content, determined to be 14.3%.

EXAMPLE 40

4.6 ml of iodine solution was added to 100 ml of 20% solution of Ficoll polymer in water, at 45° C. The temperature was maintained for one hour, with stirring. The resulting solution was cooled, filtered, and assayed for available iodine content, determined to be 9.05%.

EXAMPLE 41

7.6 ml of iodine solution was added to 100 ml of a 20% solution of Ficoll polymer in water, with stirring at 65° C. The temperature was maintained for one hour, followed by cooling of the solution and assaying for available iodine content. The available iodine content was determined to be 15.1%.

EXAMPLE 42

4.6 ml of iodine solution was added with stirring to 100 ml of a 20% Ficoll polymer solution in water, with stirring at 65° C. The temperature was maintained for one hour, with the solution then being cooled and assayed for available iodine content, which was determined to be 8.8%.

EXAMPLE 43

20 g of Ficoll polymer was dissolved in 150 cc of water. 20 cc iodine solution which was prepared according to Example 10 was then added to the clear Ficoll polymer solution with stirring. The resulting solution was then stirred for an additional one-half hour, filtered, and the resulting Ficoll-iodine iodophor complex was freeze dried to form a fine powder. The available iodine content was assayed to be 24%.

EXAMPLE 44

1.39 g of polydextrose-iodine complex with 7.0% available iodine content was dissolved in 50 cc of water. 30 g of glycerin, 0.06 g of buffer (prepared by mixing and grinding 15 g of disodium phosphate and 71 g of anhydrous citric acid), and 0.25 g of polysorbate 80, were all added to the clear solution of PDI. The components were all thoroughly dissolved in the solution, which was then quantitatively transferred to a 100 ml volumetric flask, and raised to the 100 ml volume by addition of distilled water. The resulting solution was assayed for available iodine content, which was determined to be 0.1% by weight/volume.

EXAMPLE 45

1.39 g of polydextrose-iodine complex (PDI) having a 7.0% available iodine content, is dissolved in 50 ml of water. 1 g of glycerin, 0.06 g of buffer prepared as outlined in Example 44, and 0.25 g of polysorbate 80 are all added to the PDI solution. The components are all thoroughly dissolved, with the solution quantitatively transferred to a 100 ml volumetric flask, with the volume thereof being raised to 100 ml by the addition of distilled water. The available iodine content that was assayed, was found to be 0.1% weight/volume of solution.

EXAMPLE 46

27.78 g of polydextrose iodine complex having a 7.07% available iodine content, was dissolved in 50 ml of water, with 30 g of glycerin, 0.25 g of Alipal CO-436, 1.119 g of buffer being added thereto. All components were thoroughly dissolved, with the solution quantitatively transferred to a 100 ml volumetric flask. The solution volume was raised to 100 ml by the addition of more water. The available iodine content that was assayed, was determined to be 2.0%.

EXAMPLE 47

13.89 g of polydextrose iodine complex was dissolved in 50 ml of water. 30 g of glycerin, 0.25 g of Alipal CO-436 and 0.56 g of buffer, were all added to the solution, which was then quantitatively transferred to a 100 ml volumetric flask. The volume of the solution was then raised to 100 ml by the addition of more water. The available iodine content of the resulting solution was determined to be 1.0%.

EXAMPLE 48

3.47 g of polydextrose iodine complex having 7.07% available iodine content, is dissolved in 50 ml of water. 30 g of glycerin, 0.25 g of Alipal CO-436, and 0.14 g of buffer, are all then added and dissolved in the PDI complex solution. The solution is quantitatively transferred to a 100 ml volumetric flask, with the volume thereof being raised to 100 ml by the further addition of water. The available iodine content was assayed at 0.25%.

EXAMPLE 49

1.39 g of polydextrose iodine complex was dissolved in 50 ml of water. 30 g of glycerin, 0.25 g of Alipal CO-436, and 0.14 g of buffer are all added and dissolved in the PDI solution. The solution was then quantitatively transferred to a 100 ml volumetric flask, and raised to 100 ml volume by addition of more water. The available iodine content therein was determined to be 0.1%.

EXAMPLE 50

13.95 g of polydextrose iodine complex was dissolved in 50 cc of water. 1 g of glycerin, 0.25 g of Alipal CO-436, and 0.56 g of buffer were all then added to the PDI solution. The solution was transferred quantitatively to 100 ml volumetric flask, where water was then added to raise the volume of the solution to 100 ml. The available iodine content was determined to be 1%.

EXAMPLE 51

13.95 g of polydextrose iodine complex was dissolved in 50 ml of water. 1 g of glycerin, 0.25 g of Alipal CO-436, and 0.056 g of buffer were all then added to the PDI complex. The resulting solution was quantitatively transferred to a 100 ml volumetric flask, where the overall volume of the solution being raised to 100 ml by addition of more water. The available iodine content was determined to be 0.1%.

EXAMPLE 52

14.1 g of polydextrose iodine complex, having a 7.0% available iodine content, 1 g of glycerin, and 0.25 g of Hamposyl L-30 (surfactant) (available as a 30% solution) are all dissolved in about 80 ml of water. 0.914 g of buffer was added portionwise to the solution until the pH thereof was in the range of 4.9–5.1. The solution was then quantitatively transferred to a 100 ml volumetric flask, with the volume of solution being raised to 100 ml by addition of more water. The final pH of the solution was determined to be 5.01, with the available iodine content therein determined as 1%.

EXAMPLE 53

14.1 g of polydextrose iodine complex, 1 g of glycerin, and 0.3 g ammonium myrth sulfate (available with a 60% concentration), are all dissolved in about 80 ml of water. Citric acid/disodium phosphate buffer prepared according to Example 44, was added portionwise to lower the pH to 5.01. The solution was then quantitatively transferred to a 100 ml flask, with the volume of solution being raised by addition of more water to 100 ml. The final pH of the composition was determined to be 5.0, with the available iodine content being 1%.

EXAMPLE 54

14.1 g of polydextrose iodine complex having a 7.0% available iodine content, 1 g of glycerin, and 0.25 g of Mirataine CBS (surfactant), are dissolved in about 80 ml of water, with buffer being added portionwise, until the pH is lowered to 5.0. The solution is then quantitatively transferred to a 100 ml volumetric flask, with the volume thereof being raised to 100 ml by addition of more water. The final pH of the composition was determined to be 5.0, with the available iodine content being 1%.

EXAMPLE 55

14.0 g of polydextrose iodine complex, 1.0 g of glycerin, and 0.25 g of Hamposyl TL-40 (surfactant), are dissolved in approximately 80 ml of water. Citric acid/disodium phosphate buffer prepared according to Example 44 is added portionwise to the solution until the pH is lowered to 5.5. A few drops of 10% hydrochloric acid are then added dropwise to further lower the pH of the solution to 5.0. The solution is then quantitatively transferred to a 100 ml flask, where more water is added to raise the volume of solution to the concomitant 100 ml level. The available iodine content was determined to be 1.0%, with the pH of the solution being 5.0.

EXAMPLE 56

5 cc of iodine solution prepared according to Example 10, was added to 20 g of polydextrose polymer dissolved in 100 cc of water, with stirring. The resulting solution was heated to 55° C., and the temperature maintained at the level for one hour. The solution was then cooled over ice, filtered, assayed, and then freeze-dried. The freeze-dried product was further assayed. The analysis resulted in a determination of 8.69% available iodine content of the liquid assayed before freeze-drying, and 8.15% available iodine content of the solid powder after freeze-drying.

EXAMPLE 57

12 cc of iodine solution containing 621,81 mg $I_2$/cc and prepared according to Example 10, was added with stirring to 20 g of polydextrose polymer that was dissolved in 100 cc of water. The resulting solution was heated to 55° C., with the temperature being maintained for one hour. The liquid polydextrose iodine (PDI) complex was assayed, and cooled, filtered, and freeze dried, with the freeze-dried product also being assayed. The assay of the liquid solution resulted in a determination of 18.6% available iodine content, with the assay of the freeze-dried product determining 17.05% available iodine content, after freeze-drying.

EXAMPLE 58

4 cc of iodine solution prepared according to Example 10 was added with stirring to 20 g of Ficoll 400 polymer dissolved in 100 cc of water. The solution was heated to 55° C., with the temperature being maintained at the level for one hour. The Ficoll polymer iodine complex solution was cooled, filtered, freeze-dried, and then assayed for available iodine content, determined to be 9.25%.

EXAMPLE 59

400 ml of iodine solution was added with stirring to 20 g of Ficoll polymer dissolved in 100 cc of water. The solution was heated to 55° C., with the temperature being maintained at that level for one hour. The solution was then cooled, filtered, freeze-dried, and assayed for available iodine content determined to be 8.91%.

EXAMPLE 60

600 g of polydextrose was dissolved in 3,000 cc of water with vigorous stirring, until a clear solution was obtained. 71 cc of an iodine solution containing 63 g $I_2$, was then added to the clear solution with stirring. The resulting batch was heated to 55° C., with the temperature maintained at that level for one hour. The batch was then cooled to room temperature and filtered. The liquid product was freeze-dried, with the freeze-dried solid product then being assayed for available iodine, determined to be 3.25%.

EXAMPLE 61

600 g of polydextrose was dissolved in 3,000 cc of water with vigorous stirring, until a clear solution was obtained. 155 cc of iodine solution prepared from 137 g $I_2$, was then added to the polydextrose solution with stirring. The resulting batch was heated to 55° C., with the temperature maintained at that level for one hour.

The solution was then cooled to room temperature and filtered. The PDI complex can be used in the liquid form, however it is preferably freeze-dried to obtain the solid form of the PDI complex. The PDI complex was so freeze-dried, and assayed for available iodine content, which was determined to be 7.45%.

EXAMPLE 62

82 g potassium iodide (KI) was dissolved in 200 cc of water. Iodine ($I_2$) was added, with stirring for one hour at room temperature. The resulting solution was filtered and assayed for available iodine content, which was determined to be 888.44 mg $I_2$/cc.

This iodine solution was used in the preparation of the various PDI complexes, and Ficoll polymer-iodine complexes, noted supra.

EXAMPLE 63

10 g polydextrose and 2 g iodine (particle size 40 mesh) were thoroughly mixed and placed in a 4 oz. wide-mouth jar. 0.12 cc water was then added by syringe, and the jar was capped. The mixture was shaken for 24 hours. No apparent reaction was noted between the polydextrose and iodine crystals added therein.

EXAMPLE 64

10 g polydextrose and 2 g elemental iodine were thoroughly mixed and placed in a 4 oz. wide-mouth jar. 0.63 cc water was added by syringe, and the jar capped. The mixture was shaken for 24 hours. No apparent reaction was noted.

EXAMPLE 65

10 g polydextrose and 2 g elemental iodine were thoroughly mixed placed in a 4 oz. wide-mouth jar. 1.33 cc water was added by syringe, and the jar capped. The mixture was shaken for 24 hours. The formation of a polydextrose-water gel was observed. The gel had a greenish tinge. However, iodine crystals were visible within the gel, and no apparent reaction took place.

The preceding description of the present invention is merely intended as exemplary, and is not intended to limit the scope thereof in any way, shape, or form.

What is claimed is:

1. A germicidal complex of iodine with the copolymer of sucrose and epichlorohydrin, said copolymer having an average molecular weight of 400,000±100,000 and wherein the amount of iodine is up to 20%.

2. The germicidal complex according to claim 1 wherein the amount of iodine is about 2-10%.

3. A germicidal and bactericidal composition comprising a carrier for topical application having the complex of claim 1 distributed therein.

4. The composition according to claim 3 and also including a surfactant.

5. The composition of claim 4 and also including a buffer.

* * * * *